(12) United States Patent
Chapman et al.

(10) Patent No.: US 7,543,985 B2
(45) Date of Patent: Jun. 9, 2009

(54) VIRTUAL PIVOT FOR A RADIOGRAPHIC ASSEMBLY

(75) Inventors: Raymond P. Chapman, Fairport, NY (US); Michael P. Simunek, Penfield, NY (US)

(73) Assignee: Carestream Health, Inc., Rochester, NY (US)

( * ) Notice: Subject to any disclaimer, the term of this patent is extended or adjusted under 35 U.S.C. 154(b) by 10 days.

(21) Appl. No.: 11/741,790

(22) Filed: Apr. 30, 2007

(65) Prior Publication Data

US 2008/0267357 A1   Oct. 30, 2008

(51) Int. Cl.
*G03B 42/02* (2006.01)
(52) U.S. Cl. ...................... 378/181; 378/189
(58) Field of Classification Search ................. 378/181, 378/189–191
See application file for complete search history.

(56) References Cited

U.S. PATENT DOCUMENTS

| 6,128,135 | A | * | 10/2000 | Stiles et al. | .................. 359/597 |
| 6,851,851 | B2 | * | 2/2005 | Smith et al. | .................. 378/189 |
| 2004/0244788 | A1 | * | 12/2004 | Register | .................. 125/13.01 |
| 2004/0245420 | A1 | * | 12/2004 | Pfister et al. | ............ 248/289.11 |
| 2005/0046290 | A1 | * | 3/2005 | Baukholt et al. | .......... 310/75 R |
| 2005/0226391 | A1 | * | 10/2005 | Sekol et al. | .................. 378/197 |
| 2006/0061179 | A1 | * | 3/2006 | Brendel et al. | ......... 297/354.12 |
| 2008/0069308 | A1 |   | 3/2008 | Chapman |   |

* cited by examiner

*Primary Examiner*—Edward J Glick
*Assistant Examiner*—Mona M Sanei (57) ABSTRACT

A radiographic apparatus is provided for rotating a radiographic assembly about a virtual pivot axis. The apparatus includes a structure for mounting a radiographic assembly having an x-radiation sensitive element for rotation about a pivot axis coincident with the center line of the element, wherein the structure mounts the assembly at a location other than at the pivot axis and a drive drivingly coupled to the structure for rotating the structure and the mounted radiographic assembly about the pivot axis, wherein the drive is also located at a location other than at the pivot axis.

5 Claims, 9 Drawing Sheets

VIRTUAL PIVOT FOR A RADIOGRAPHIC ASSEMBLY

FIELD OF THE INVENTION

This invention relates in general to the field of radiography and relates more specifically to an apparatus for mounting a radiographic assembly for pivoting about a virtual pivot axis.

BACKGROUND OF THE INVENTION

In projection radiography, an x-ray image of an object, such as an anatomical structure of a patient, is produced by passing x-rays from an x-ray source through the object to an x-ray sensitive radiographic assembly. The radiographic assembly includes an x-radiation sensitive element, such as screen/film, a computed radiography imaging plate, or a direct digital radiographic image receptor. The object which holds the x-radiation sensitive element is called a "bucky". Typically, the radiographic assembly also includes a lead grid located between the object and the radiation sensitive element to absorb scattered x-ray photons, which can blur the image, before they reach the radiation sensitive element.

Figure 1:
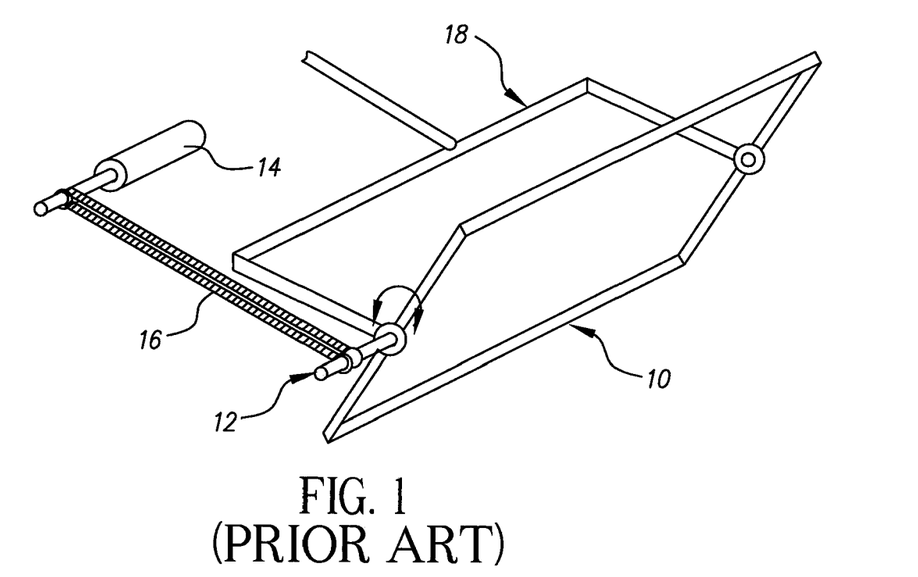
FIG. 1 is a diagrammatic view of a prior art apparatus for mounting a radiographic assembly for rotation about a pivot axis coincident with a centerline of the radiographic assembly.

In certain applications, such as for chest x-rays, the radiographic assembly, including the bucky, are pivotally mounted to allow different x-ray images to be produced of the object being x-rayed. Referring to FIG. 1, typically, the radiographic assembly 10 would be mounted so that the drive shaft or pivot axis 12 would be mounted at the center of rotation and would be driven by motor drive 14 and belt 16 about that axis. A mounting structure or frame 18 would be required at the pivot axis to support the radiographic assembly 10. Due to space constraints and patient use, it is not desirable to place the drive or the mount at the actual center of rotation of the radiographic assembly. This would interfere with patient access and use.

There is thus a need for a mounting and drive system for a pivotable radiographic assembly that provides a solution to these problems.

SUMMARY OF THE INVENTION

According to an aspect of the present invention, there is provided a radiographic apparatus comprising: a structure for mounting a radiographic assembly having an x-radiation sensitive element for rotation about a pivot axis coincident with the center line of said element, wherein said structure mounts said assembly at a location other than at said pivot axis and a drive drivingly coupled to said structure for rotating said structure and said mounted radiographic assembly about said pivot axis, wherein said drive is also located at a location other than at said pivot axis.

The invention has some advantages. The radiographic assembly is mounted at a location other than the pivot axis of the assembly, constraining all of the degrees of freedom except the rotation about the assembly centerline. The drive for rotating the radiographic assembly is at a location other than the pivot axis while maintaining the radiographic assembly at the center of rotation. This results in meeting space constraint requirements and patient use requirements.

DETAILED DESCRIPTION OF THE INVENTION

In general, the present invention relates to projection radiography where a radiographic assembly, called a "bucky", is rotatable about a pivot axis. The bucky includes an x-radiation sensitive element and a lead grid. The x-radiation sensitive element can be a screen/film, a computed radiography imaging plate or a direct digital radiographic image receptor. The lead grid is interposed between a patient and the x-radiation sensitive element and is typically moved during x-ray exposure. In order to meet space requirements and patient requirements, the radiographic assembly is mounted for rotation about a virtual pivot axis which is coincident with the center line of the x-radiation sensitive element. Both the mounting structure and the rotational drive are located at a location other than at the pivot axis.

Figure 2:
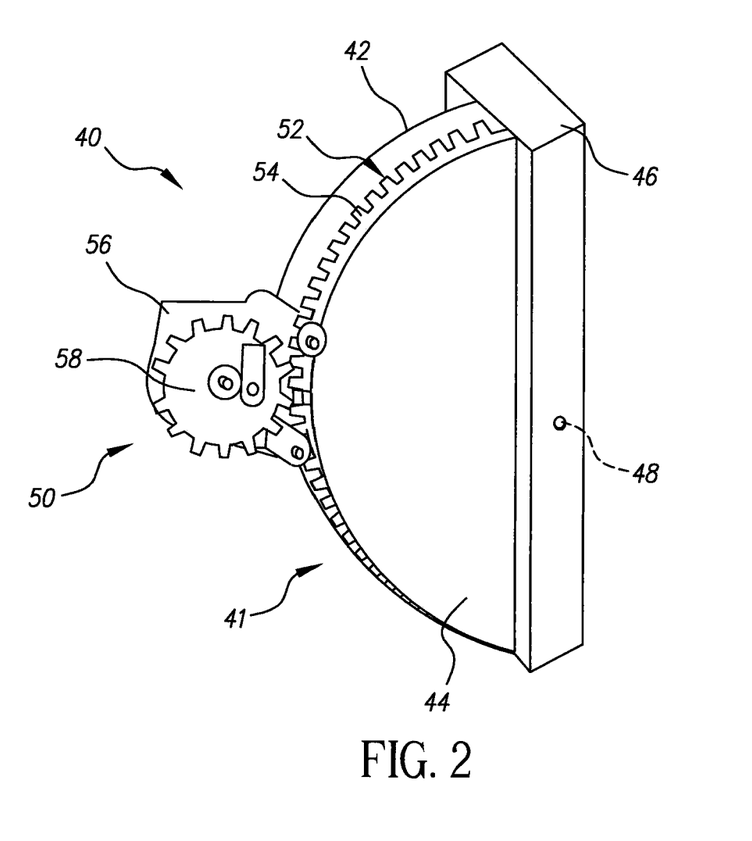
FIG. 2 is a perspective, diagrammatic view of an embodiment of the present invention.

FIG. 2 shows an embodiment of the present invention. Only essential elements are shown and it will be understood that other structural elements for mounting and enclosing the shown elements to make a functional product are within the scope of one skilled in the art and need not be shown here. Apparatus 40 includes structure 41 having a pair of spaced circular segments 42 and 44 which mount radiographic assembly 46 for rotation about pivot axis 48 which is coincident with the center line of an x-radiation sensitive element contained in assembly 46. Segments 42 and 44 have centers which coincide with the pivot axis. A drive 50 for rotating structure 41 includes a circular segment gear 52 having teeth 54 about the periphery of gear 52, a motor 56, and a drive gear(s) 58 driven by motor 56 which meshes with gear 52. Gear 52 has a center coincident with the pivot axis 48. It will be understood that more than two segments can be used to support radiographic assembly 46, and that more than one gear 54 or 58 can be used. Rollers 60 and 62 are shown (along with others not shown) near the gear drive to hold the gears in mesh and to keep the assembly together. Both the mounting structure and drive are located at locations other than at the pivot axis. This meets space constraint requirements and patient use requirements. As an example, when a patient has a chest x-ray, typically the patient is asked to press against the bucky and hug it. If the assembly is rotatable about the center line of the assembly, the drive for the assembly can interfere with this action by the patient. The present invention solves this problem by locating the pivot mounting structure and drive away from the side edges of the radiographic assembly.

Figure 3:
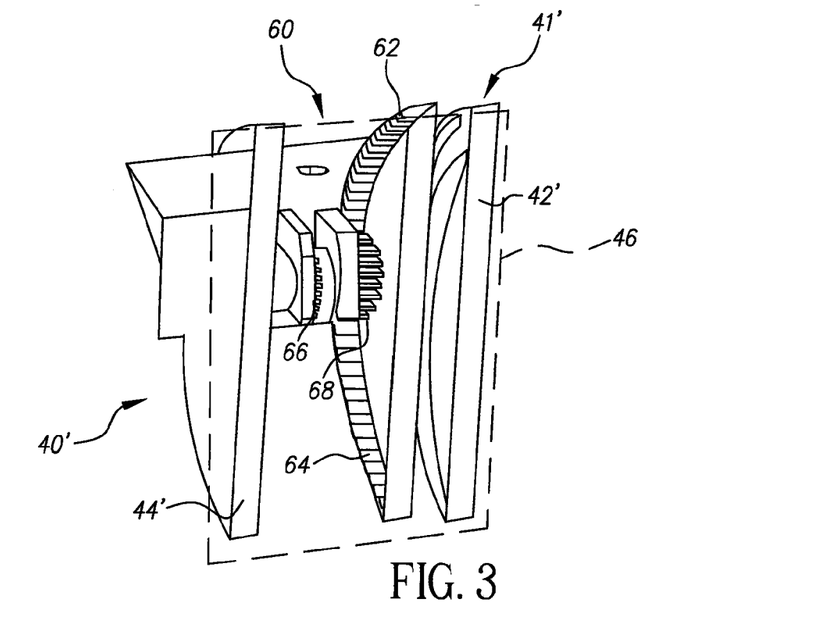
FIG. 3 is a perspective, diagrammatic view of another embodiment of the present invention.

FIG. 3 shows an embodiment of the present invention similar to that shown in FIG. 2. Apparatus 40' includes structure 41' having spaced circular segments 42' and 44' for mounting radiographic assembly 46. Drive 60 includes a circular segment gear 62 having internal planetary teeth 64. Motor 66 and drive gear 68 are mounted internally of structure 41'. Motor 66 drives gear 68 which meshes with gear 62 to rotate it.

Figure 4:
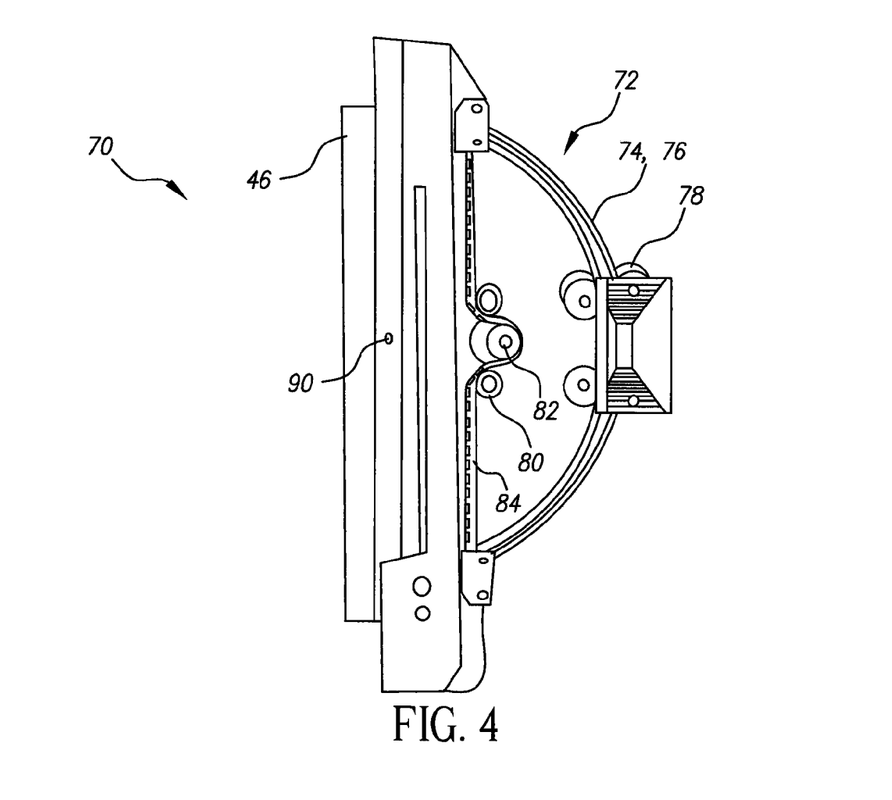
FIG. 4 is a perspective, diagrammatic view of a further embodiment of the present invention.

FIG. 4 shows another embodiment of the present invention. As shown, apparatus 70 includes a structure 72 having spaced, partially circular rods 74 and 76 mounted by roller assembly 78. Rods 74 and 76 mount radiographic assembly 46 having an x-radiation sensitive element. A drive 80 is mounted internally of structure 72 and includes a motor 82 and timing belt 84 connected to rods 74, 76. Motor 82 drives belt 84 which rotates rods 74, 76 about virtual pivot axis 90, which is coincident with the x-radiation sensitive element. Rods 74, 76 have centers which are coincident with pivot axis 90.

Figure 5:
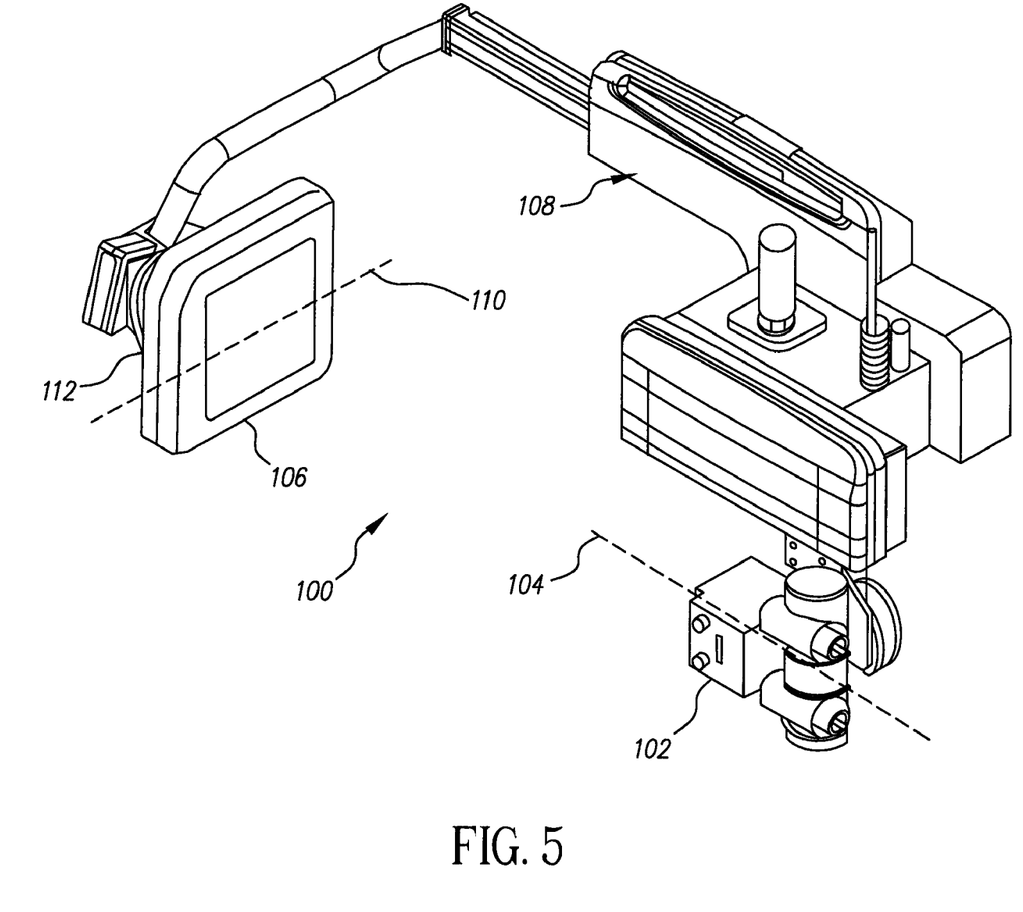
FIGS. 5-7 are diagrammatic views showing an x-ray system incorporating the present invention.
Figure 6:
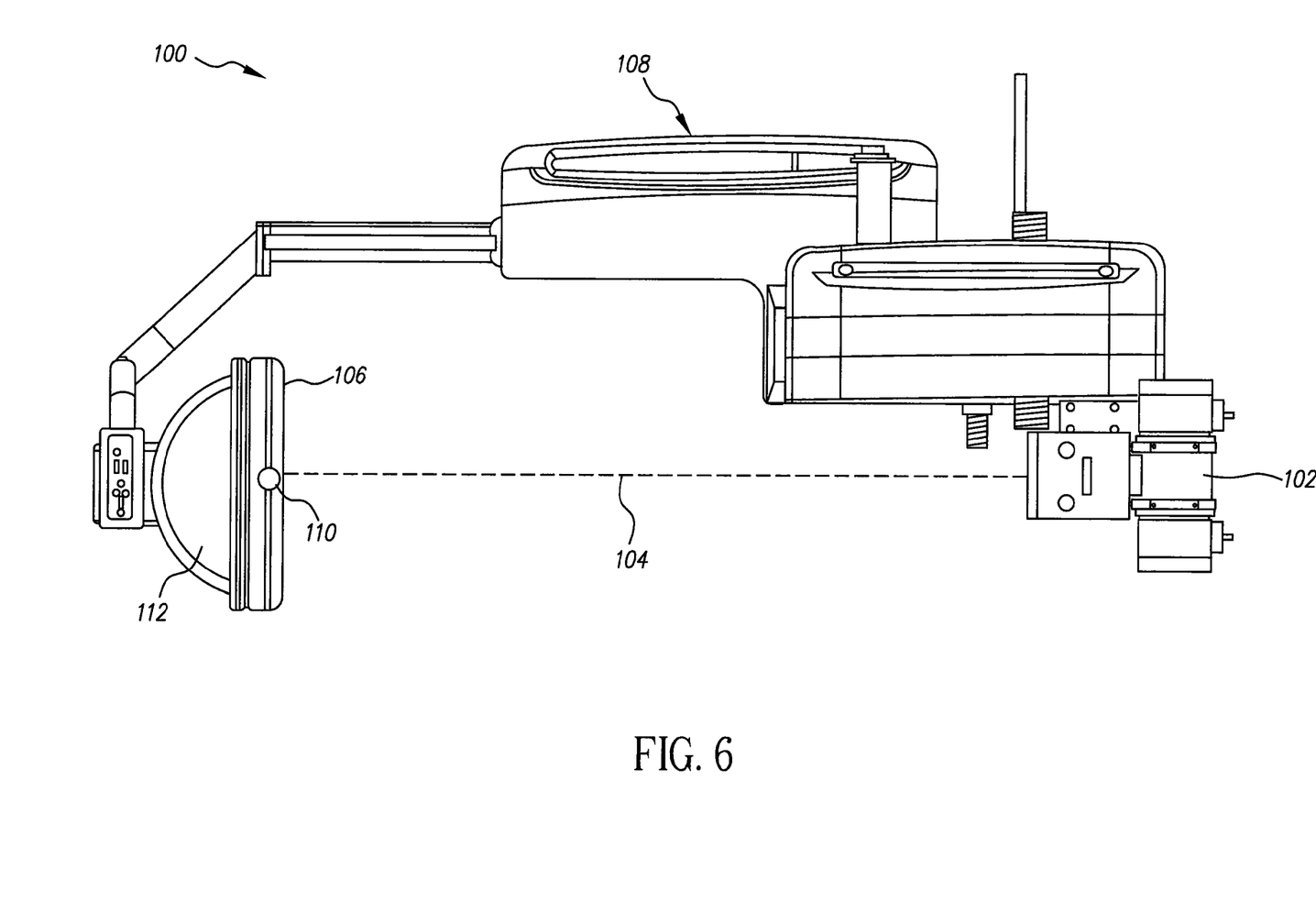
Figure 7:
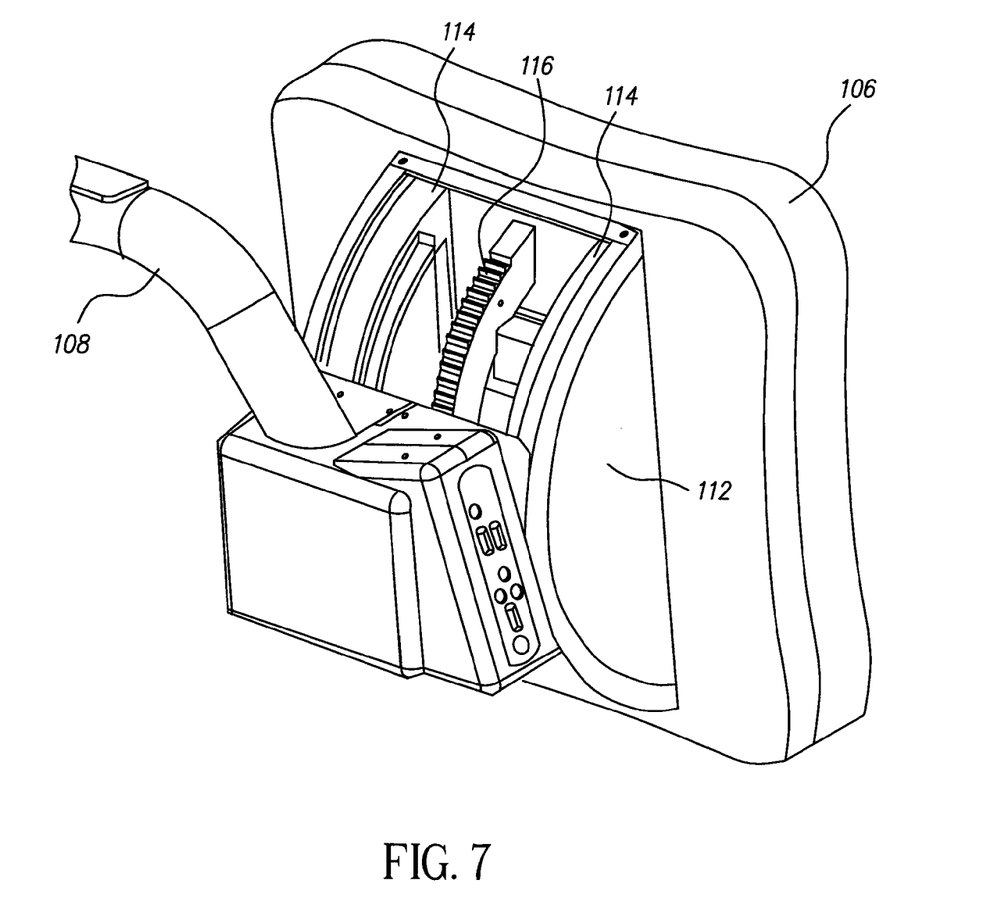

FIGS. 5-7 show an x-ray system incorporating an embodiment of the present invention. As shown, x-ray system 100 includes a source of x-rays 102 which projects x-radiation along axis 104 to radiographic assembly 106 which is mounted on a movable boom 108. Assembly 106 is mounted for rotation about virtual pivot axis 110 by structure 112. FIG. 7 shows structure 112 in greater detail which includes circular segments 114 having center lines coincident with the pivot axis 110, and gear drive 116.

Figure 8A:
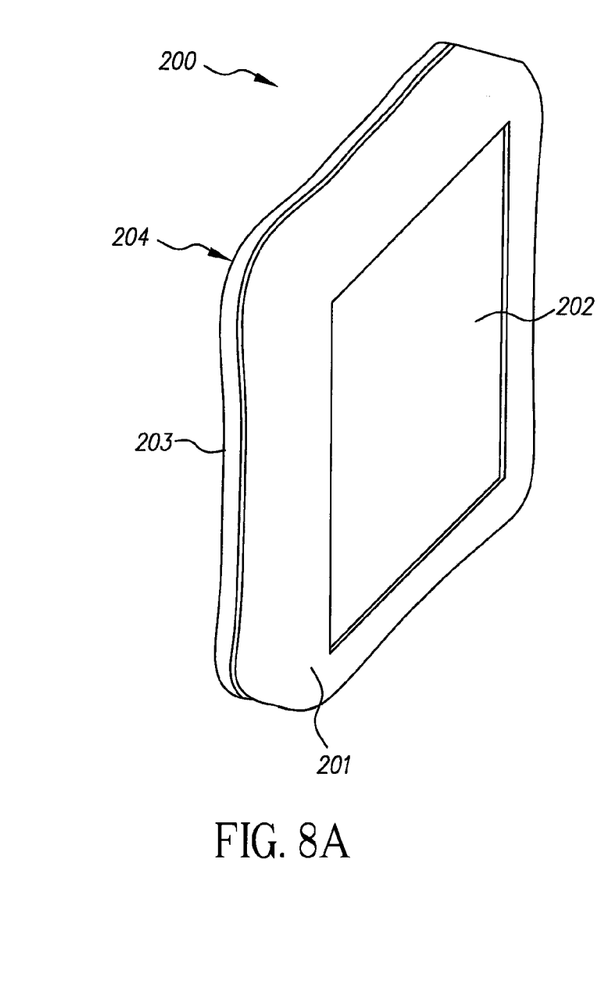
FIGS. 8A-8D are diagrammatic views showing an exemplary radiographic assembly.
Figure 8B:
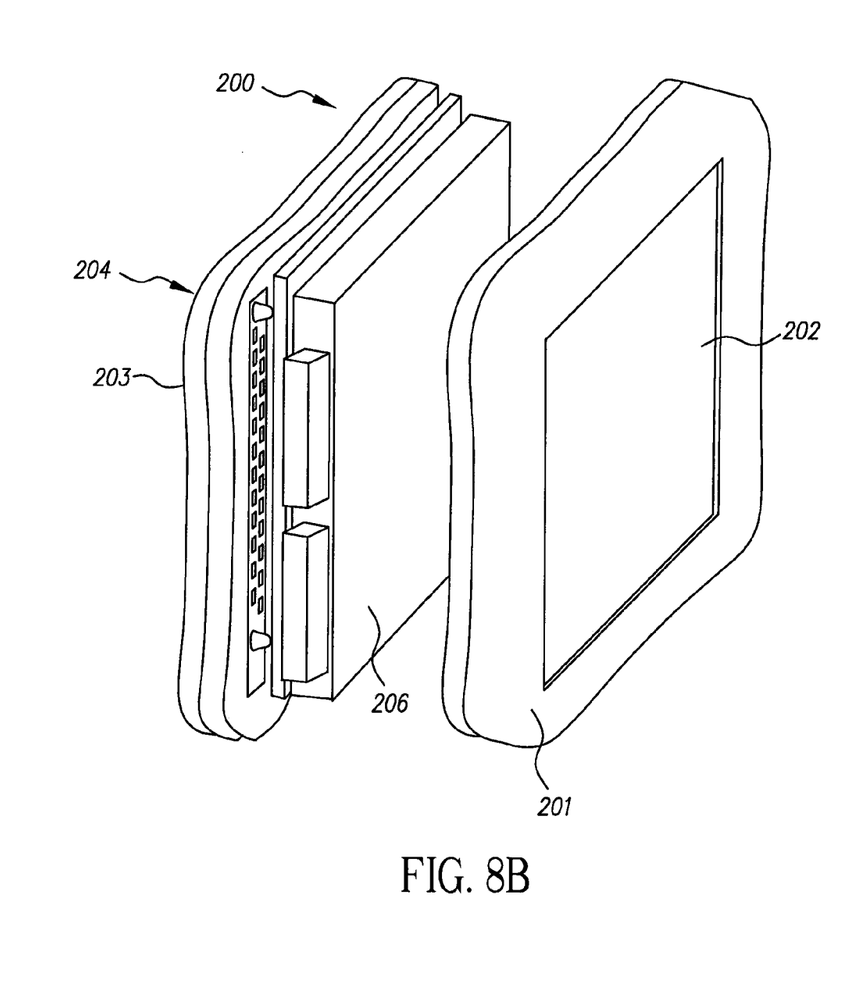
Figure 8C:
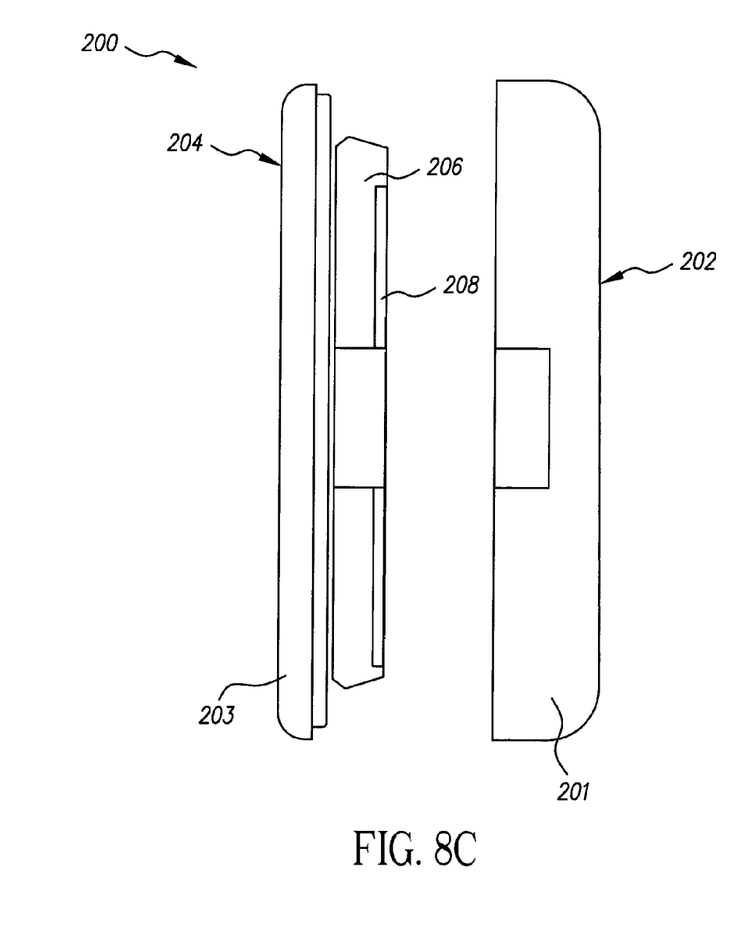
Figure 8D:
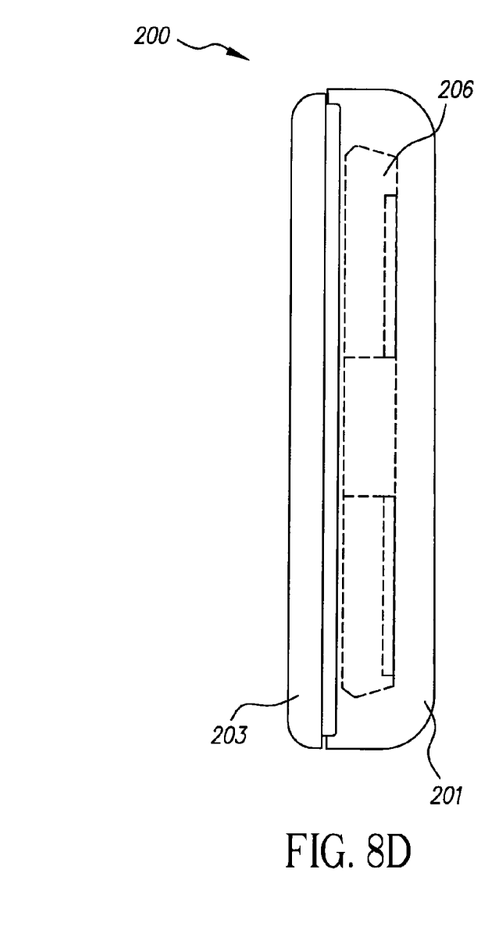

FIGS. 8A-8D show an exemplary radiographic assembly. FIG. 8A shows radiographic assembly 200 in a closed position. Assembly 200 has a front cover 201 having front face 202 facing the x-ray source and a rear member 203 having rear face 204. FIG. 8B shows radiographic assembly 200 in an open position showing x-radiation detector 206. FIG. 8C shows detector 206 with its image plane 208 being the front face of detector 206. FIG. 8D shows radiographic assembly 200 with the front cover translucent to show the positioning of detector 206 inside assembly 200.

Figure 9A:
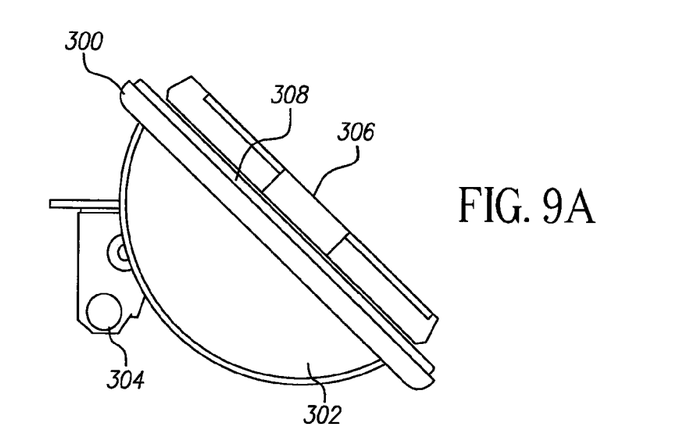
FIGS. 9A-9C and 10A-10C are diagrammatic views useful in explaining the operation of the present invention.
Figure 9B:
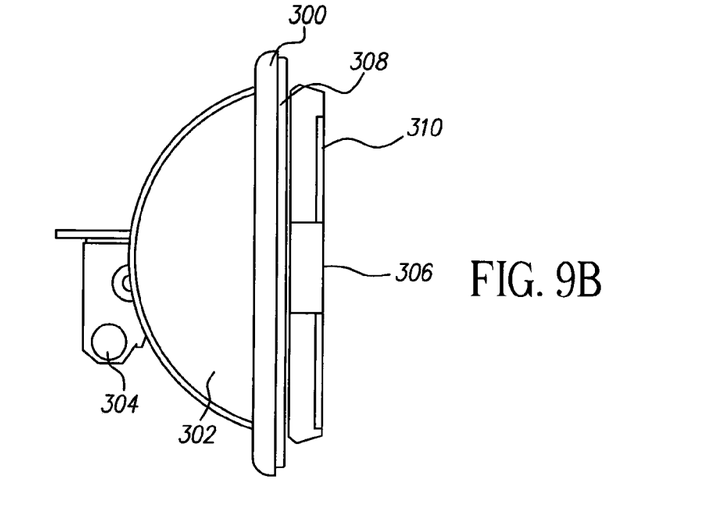
Figure 9C:
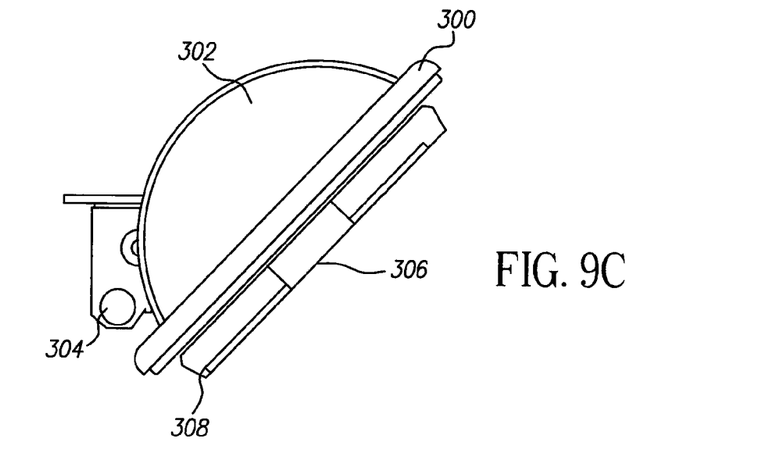

FIGS. 9A-9C show radiographic assembly 300 mounted on rotatable structure 302 driven by drive 304. Assembly 300 is similar to assembly 200 in FIGS. 8A-8D but is shown with the front cover off. Pivot point 306 is shown located at the centerline of the image plane 310 of detector 308. FIG. 9A shows the assembly 300 at its maximum tilt position, FIG. 9B shows assembly 300 in its intermediate position, and FIG. 9C shows assembly 300 at its minimum tilt position.

Figure 10A:
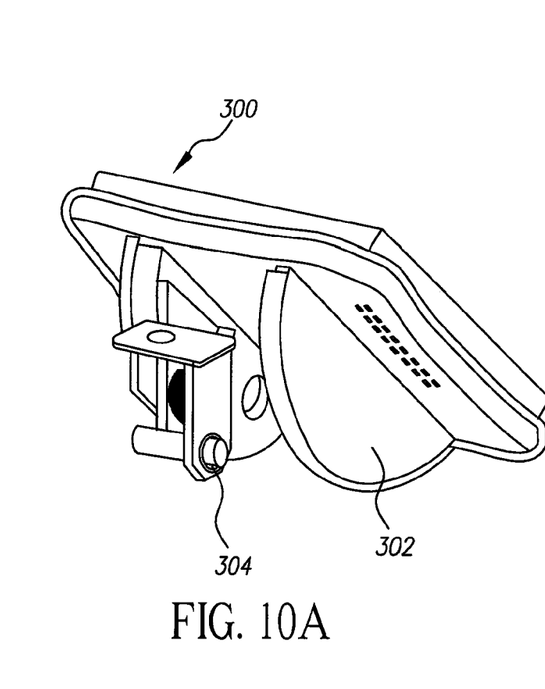
Figure 10B:
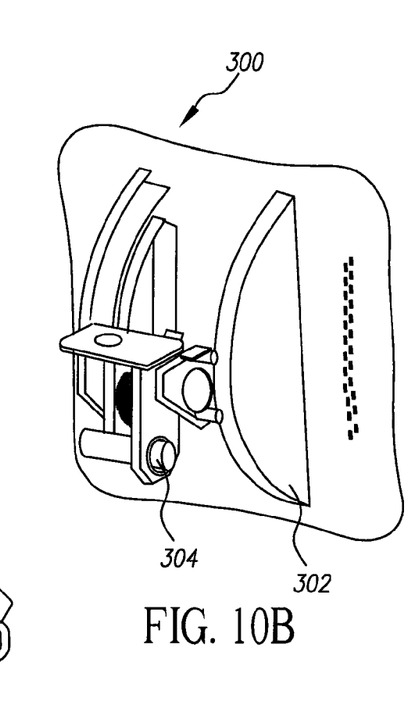
Figure 10C:
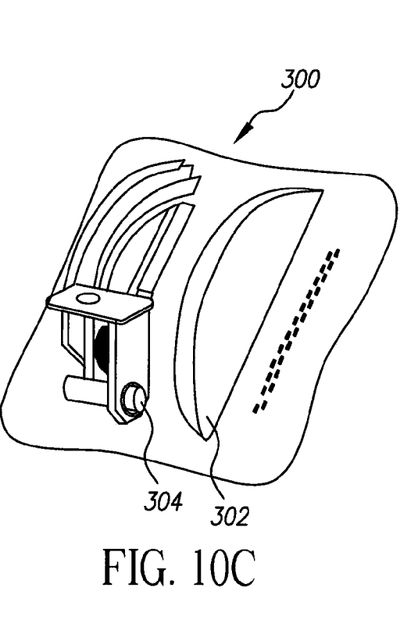

FIGS. 10a-10C show the radiographic assembly of FIGS. 9A-9C from the rear. FIG. 10A corresponds to FIG. 9A and shows the assembly at its maximum tilt position, FIG. 10B corresponds to FIG. 9B and shows the assembly at its intermediate position, and FIG. 10C corresponds to FIG. 9C and shows the assembly at its minimum tilt position.

The invention has been described in detail with particular reference to, certain preferred embodiments thereof, but it will be understood that variations and modifications can be effected within the spirit and scope of the invention.

PARTS LIST

10—radiographic assembly, bucky
12—drive shaft, pivot axis
14—motor drive
16—belt
18—mounting structure or frame
40—apparatus
40'—apparatus
41—structure
41'—structure
42, 44—circular segments
42', 44'—circular segments
46—radiographic assembly/bucky
48—pivot axis
50 drive
52—circular segment gear
54—teeth
56—motor
58 drive gear assembly
60—drive
62—gear
63—circular segment gear
64—internal planetary teeth
66—motor
68—drive gear assembly
70—apparatus
72—structure
74, 76—partially circular rods
78 roller assembly
80—drive
82—motor
84—timing belt
90—virtual pivot axis
100—x-ray system
102 source of x-rays
104—axis
106—radiographic assembly
108—movable boom
110—virtual pivot axis
112—structure
114—circular segments
116—gear drive
200—radiographic assembly
201—front cover
202—front face
203—rear member
204—rear face
206—x-radiation detector
208—image plane
300—radiographic assembly
302—rotatable structure
304—drive
306—pivot point
308—detector
310—image plane

The invention claimed is:

1. A radiographic apparatus comprising:
a structure for mounting a radiographic assembly having an x-radiation sensitive element for rotation about a pivot axis coincident with the center line of the element, wherein the structure mounts the assembly at a location other than at the pivot axis; and
a drive drivingly coupled to the structure for rotating the structure and the mounted radiographic assembly about the pivot axis, wherein the drive is also located at a location other than at the pivot axis;
wherein the structure includes a plurality of spaced circular segments which mount the radiographic assembly, wherein the circular segments have centers which coincide with the pivot axis;
wherein the drive includes a circular segment gear having gear teeth about the periphery of the gear and a center coincident with the pivot axis;
wherein the drive includes a motor and drive gear assembly which mesh with the circular segment gear; and
wherein the drive is mounted external to the structure.

2. The apparatus of claim 1 wherein the radiographic assembly includes a lead grid.

3. The apparatus of claim 2 wherein the radiographic assembly includes one of a screen/film, a computed radiography imaging plate, and a direct digital radiographic image receptor.

4. A radiographic apparatus comprising:

a structure for mounting a radiographic assembly having an x-radiation sensitive element for rotation about a pivot axis coincident with the center line of the element, wherein the structure mounts the assembly at a location other than at the pivot axis; and a drive drivingly coupled to the structure for rotating the structure and the mounted radiographic assembly about the pivot axis, wherein the drive is also located at a location other than at the pivot axis;

wherein the structure includes a plurality of spaced circular segments which mount the radiographic assembly, wherein the circular segments have centers which coincide with the pivot axis;

wherein the drive includes a circular segment gear having planetary gear teeth mounted internally of the gear and a center coincident with the pivot axis; and wherein the drive includes a motor and drive gear assembly which mesh with the planetary gear teeth; and wherein the drive is located internal to the structure.

5. A radiographic apparatus comprising:

a structure for mounting a radiographic assembly having an x-radiation sensitive element for rotation about a pivot axis coincident with the center line of the element, wherein the structure mounts the assembly at a location other than at the pivot axis; and a drive drivingly coupled to the structure for rotating the structure and the mounted radiographic assembly about the pivot axis, wherein the drive is also located at a location other than at the pivot axis;

wherein the structure includes a plurality of spaced partially circular rods, a roller assembly for mounting the rods;

wherein the rods have centers coincident with the pivot axis and mount the radiographic assembly; and wherein the drive includes a motor and belt assembly mounted internal to the rods.

* * * * *